(12) United States Patent
Rock et al.

(10) Patent No.: US 8,362,255 B2
(45) Date of Patent: Jan. 29, 2013

(54) PROCESS FOR THE MANUFACTURE OF [PHENYLSULFANYLPHENYL]PIPERIDINES

(75) Inventors: Michael Rock, Hvidovre (DK); Sebastian Brandes, Roskilde (DK)

(73) Assignee: H. Lundbeck A/S, Copenhagen-Valby (DK)

( * ) Notice: Subject to any disclaimer, the term of this patent is extended or adjusted under 35 U.S.C. 154(b) by 0 days.

(21) Appl. No.: 12/920,357

(22) PCT Filed: Mar. 2, 2009

(86) PCT No.: PCT/EP2009/052440
§ 371 (c)(1), (2), (4) Date: Oct. 8, 2010

(87) PCT Pub. No.: WO2009/109541
PCT Pub. Date: Sep. 11, 2009

(65) Prior Publication Data
US 2011/0054178 A1     Mar. 3, 2011

Related U.S. Application Data

(60) Provisional application No. 61/033,093, filed on Mar. 3, 2008.

(30) Foreign Application Priority Data

Mar. 3, 2008   (DK) .............................. 2008 00314

(51) Int. Cl.
*C07D 211/06* (2006.01)

(52) U.S. Cl. .................. 546/218; 546/217; 546/236
(58) Field of Classification Search ................ None
See application file for complete search history.

(56) References Cited

U.S. PATENT DOCUMENTS

| | | | |
|---|---|---|---|
| 5,929,243 A * | 7/1999 | Askin et al. ................ 546/227 |
| 7,732,463 B2 | 6/2010 | Puschl et al. | |
| 2005/0014740 A1 * | 1/2005 | Ruhland et al. .......... 514/212.01 |
| 2006/0084662 A1 | 4/2006 | Ruhland et al. | |

FOREIGN PATENT DOCUMENTS

| WO | 0146147 | 6/2001 |
| WO | 03029232 | 4/2003 |
| WO | 2007144006 | 12/2007 |

OTHER PUBLICATIONS

Palmer et al., Probing the Active Sites of Monoamine Oxidase A and B with 1,4-Disubstituted Tetrahydropyridine Substrates and Inactivators, 40 J. Med. Chem. 1982-1989 (1997).*

Mendez et al., An Efficient Synthesis of New 1-H-4'-methyl-3',4'-dihydrospiro[piperidine-4,2'(1'H)quinoline scaffolds, 48 Tetrahedron Letts. 2509-2512 (2007) (Published on the web Feb. 2007).*

Schopfer et al., A General Palladium-Catalysed Synthesis of Aromatic and Heteroaromatic Thioethers, 57 Tetrahedron 3069-3073 (2001).*

* cited by examiner

*Primary Examiner* — Janet Andres
*Assistant Examiner* — Timothy R Rozof
(74) *Attorney, Agent, or Firm* — Fish & Richardson P.C.

(57) ABSTRACT

A process for the manufacture of (un)substituted phenylsulfanylphenyl-piperidines comprising the use of benzyl as N-piperidine protecting group is disclosed.

18 Claims, 4 Drawing Sheets

XRDP α-form

XRDP β-form

DSC α-form

DSC β-form

PROCESS FOR THE MANUFACTURE OF [PHENYLSULFANYLPHENYL]PIPERIDINES

CROSS REFERENCE TO PRIOR APPLICATIONS

Figure 1:
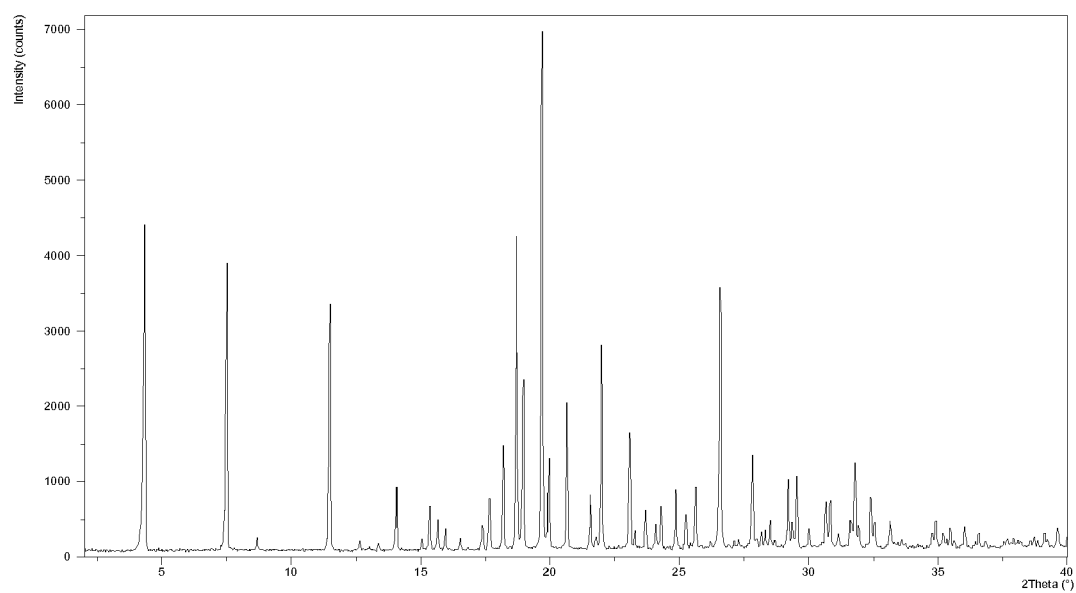

This is a U.S. National Phase application under 35 U.S.C. §371 of International Patent Application No. PCT/EP2009/052440, filed Mar. 2, 2009, and claims the priority of Danish Patent Application No. PA200800314, filed Mar. 3, 2008 and U.S. Provisional Application No. 61/033,093, filed Mar. 3, 2008. Each of the aforementioned applications is hereby incorporated herein by reference in its entirety. The aforementioned International Application published in English on Sep. 11, 2009 as WO 2009/109541 under PCT Article 21(2).

FIELD OF THE INVENTION

The present invention relates to a process for the manufacture of [phenylsulfanylphenyl]piperidines and salts thereof.

BACKGROUND OF THE INVENTION

The international patent applications published as WO 2003/029232 and WO 2007/144006 disclose that the compound 4-[2-(4-methylphenylsulfanyl)phenyl]-piperidine has a pharmacological profile encompassing inhibition of the serotonin and noradrenalin reuptake, inhibition of the serotonin receptors 2A and 3 and adrenergic receptor $\alpha_{1A}$, and that said compound and salts thereof may be useful in the treatment of a range of indications, such as depression, anxiety and pain. Consequently, there is a need for processes for the manufacture of said compound which are easy, cheap and which provide a high yield.

WO 2003/029323 discloses a process wherein a tert-butoxycarbonyl protected piperidine-4-ol is transformed into an oxalate and then reduced by means of $Bu_3SnH$ to provide the desired compound after de-protection.

WO 2007/144006 discloses a process wherein ethoxycarbonyl protected piperidine-4-ol is obtained by reacting 2-(4-tolylsulfanyl)-phenyl bromide with N-carbethoxy-4-piperidone, which product is reduced by means of $SiEt_3H/TFA$ to provide the desired compound after de-protection. The process step in which the ethoxycarbonyl protected piperidine-4-ol is obtained is run at very low temperatures, i.e. −40° C. and the reduced intermediate is difficult to isolate as it does not readily crystallise.

WO 01/46147 discloses a method for reducing N-protected piperadine-4-ol by means of $SiEt_3H/TFA$.

SUMMARY OF THE INVENTION

The present inventors have surprisingly found that the use of an optionally substituted benzyl as N-piperidine protecting group allows a process to obtain the protected piperidine-4-ol that runs at higher temperatures, that gives rise to higher overall yields, and that allows for a more easy and convenient isolation and purification of intermediates by crystallisation. Accordingly, in one embodiment, the invention relates to a process wherein a compound of formula II

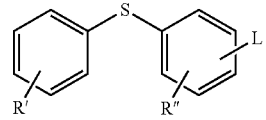

wherein R' and R" independently represent one, two or three hydrogen, halogen, $C_{1-6}$-alkyl or $C_{2-6}$-alkylene and L represents a leaving group is reacted with an optionally substituted N-benzyl-4-piperidone,

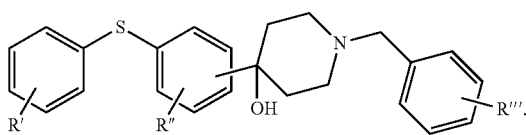

optionally in the presence of a metallation agent selected from alkyl lithium, alkyl magnesium or magnesium;
wherein R''' represents hydrogen or —O—$C_{1-6}$-alkyl to obtain a compound of formula III

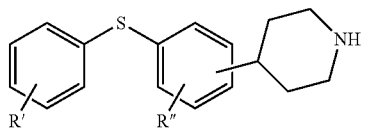

In one embodiment, the invention relates to a process for the manufacture of a compound according to formula I

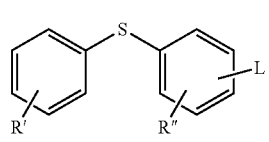

and acid addition salts thereof, said process comprising the step of reacting a compound of formula II with an optionally substituted N-benzyl-4-piperidone

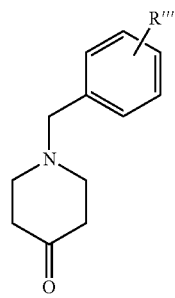

optionally in the presence of a metallation agent selected from alkyl lithium, alkyl magnesium or magnesium to obtain a compound of formula III

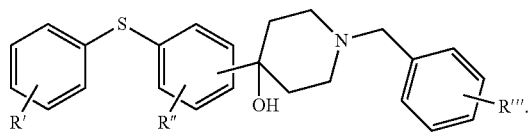

(III)

FIGURES

FIG. 1: X-Ray diffraction Pattern (XRDP) of 1-benzyl-4-hydroxy-4-[2-(4-methylphenylsulfanyl)phenyl]piperidine, HCl, α-form FIG. 2: XRDP of 1-benzyl-4-hydroxy-4-[2-(4-methylphenylsulfanyl)phenyl]piperidine, HCl, β-form FIG. 3: Differential Scanning calorimetric (DSC) of 1-benzyl-4-hydroxy-4-[2-(4-methylphenylsulfanyl)phenyl]piperidine, HCl, α-form FIG. 4: DSC of 1-benzyl-4-hydroxy-4-[2-(4-methylphenylsulfanyl)phenyl]piperidine, HCl, β-form

DETAILED DESCRIPTION OF THE INVENTION

Leaving groups are also sometimes referred to as nucleofuges, and they are typically corresponding weak bases to strong acids. Examples of leaving groups include halogens, such as Cl, Br, I, and alkyl sulfonates, such as

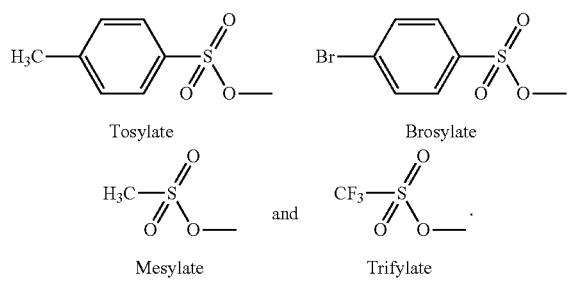

Special mention is made of Br.

In one embodiment, R' and R" are independently hydrogen or $C_{1-6}$-alkyl, such as methyl. In particular, R' is methyl and R" is hydrogen, and in particular R' is methyl in the 4-position. In one embodiment, R' and R" independently represent one or more hydrogens or halogens, such as fluoro.

In one embodiment, R''' is hydrogen or methoxy, and in particular hydrogen.

In one embodiment, the metallation agent is alkyl lithium, such as n-butyl lithium or tert-butyl lithium, and in particular n-butyl lithium.

In one embodiment, the acid addition salt is a pharmaceutically acceptable salt. In one embodiment, said acid addition are salts of acids that are non-toxic. Said salts include salts made from organic acids, such as maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, malonic, mandelic, cinnamic, citraconic, aspartic, stearic, palmitic, itaconic, glycolic, p-aminobenzoic, glutamic, benzenesulfonic, theophylline acetic acids, as well as the 8-halotheophyllines, for example 8-bromotheophylline. Said salts may also be made from inorganic salts, such as hydrochloric, hydrobromic, sulfuric, sulfamic, phosphoric and nitric acids. Special mention is made of the hydrobromic acid addition salt.

In on embodiment, one equivalent of compound II is dissolved in a suitable solvent, such as a hydrocarbon or an ethereal solvent, e.g. heptanes, tetrahydrofuran (THF) or a mixture thereof and cooled to between around −25° C. and 5° C., such as between around −10° C. and around −25° C. in a protecting atmosphere, e.g. nitrogen. Typically, between 0.1 and 4 equivalents of THF is used. To this solution is added approximately 1 equivalent of a metallation agent e.g. n-butyl lithium dissolved in a solvent such as a hydrocarbon, e.g. heptanes while maintaining the temperature below 0° C. Upon cooling to a temperature not higher than around −15° C., an optionally substituted N-benzyl-4-piperidone dissolved in a solvent, such as an etheral solvent, e.g. THF is added in an approximately equimolar amount while keeping the temperature below around −15° C. Once the addition is completed, the reaction is allowed to warm to room temperature. The product may be worked up by phase separation using a suitable solvent, such as ethyl acetate and an aqueous basic solution, e.g. NaOH with a pH around 10-12. The solvents are fully or partly removed by vacuum distillation (max temperature ~50° C.). Dissolving the product in a suitable solvent and removing said solvent e.g. by vacuum distillation may be repeated using e.g. THF as solvent. Once distillation is completed a solvent, e.g. THF is added followed by addition of an acid, for instance hydrogen chloride gas is bubbled into the solution, and the product (Compound III) is precipitated by mixing with a suitable anti-solvent, such as di-ethyl ether, and collected. As an alternative to the anti-solvent isolation/purification, seeding with crystals of compound III may be used to precipitate compound III. In order to obtain a good yield, solvents used prior to the phase separation should be dry.

As shown in the examples, the inventors have investigated the above reaction using various protecting groups, i.e. N-benzyl-4-piperidone, N-carbethoxy-4-piperidone, N-tert-butoxy-carbonyl-4-piperidone and N-benzoyl-4-piperidone and at temperatures ranging from around −15° C. to −78° C. Table 1 below summarises the yields obtained

TABLE 1

| Temperature | N-benzyl-4-piperidone | N-carboethoxy-4-piperidone | N-tert-butoxy-carbonyl-4-piperidone | N-benzoyl-4-piperidone |
|---|---|---|---|---|
| −15° C. | 90% 84% | ~30% (not isolated) | | ~0% |
| −40° C. | | 55-60% | | |
| −78° C. | | | 42% | |

It is thus evident that the use of N-benzyl-4-piperidone gives rise to a significantly higher yield and allows the reaction to be run at significantly higher temperatures. To run a reaction at −40° C., not to mention at −78° C., compared to at −15° C. requires specialised equipment and makes handling more difficult which increases the cost. Another advantage of using benzyl as protecting group is that it allows for a more convenient isolation and purification of the reaction product through crystallisation. The benzyl protected piperidine acid addition salt readily crystallises whereas the other protected piperidines do not.

Compound II may be prepared by reacting a thiophenol with a suitably substituted benzene, such as an 1,2-dihalogenbenzene in the presence of an inorganic base, such as oxides, e.g. tert-butoxide, or $Na_2CO_3$.

Alternatively, compound II may be obtained in a palladium catalysed reaction between a thiophenol and a phenyl halide [*Advanced Organic Chemistry* (1985) J. March (ed.), 589-590, John Wiley]. As an example, 4-methylthiophenol and 2-iodobromo benzene may be reacted at elevated temperature (e.g. above 80° C., such as above 100° C.) in the presence of a Pd source and a bidentate phosphine ligand. Examples of Pd sources include $PdCl_2$, $Pd(Oac)_2$ and $Pd_2dba_2$. Examples of phosphine ligands includes racemic 2,2'-bis-diphenylphosphanyl-[1,1']binaphtalenyl (rac-BINAP), 1,1'-bis(diphenylphosphino)ferrocene (DPPF), bis-(2-diphenylphosphinophenyl)ether (DPEphos); dba is dibenzylideneacetone.

In order to obtain the final product, i.e. compound (I) or acid addition salts thereof, compound III is further reacted with an alkyl chloroformate, such as ethylchloro formate followed by reduction with $Et_3SiH$/TFA. The benzylchloride released may be captured by reaction with ethanolamine. Reaction with an acid in a final step is required to remove the N-piperidine protecting group. Proper selection of said acid will afford a desired acid addition salt of compound (I) directly.

Compound III (1 equivalent) is suspended together with an excess of a base, such as $Na_2CO_3$ in a solvent, e.g. ketones, acetates, chlorinated alkyls, or aromats, such as acetone or toluene, and 2-3 equivalents of a alkylchloro formate, e.g. ethylchloro formate are added. The product may be isolated by phase separation adding water and a solvent, such as toluene or dichloromethane, and isolating the organic phase upon which the solvent is removed fully or partly, e.g. by distillation. The resulting product is added to a mixture of TFA and $Et_3SiH$ (2-3 equivalents) at a temperature between around −10° C. and around −25° C. After the reaction is completed, the mixture is allowed to warm to room temperature, and the product may be isolated by phase separation using water and a solvent, such as toluene or dichloromethane. After removing the solvents, e.g. by distillation, an appropriate acid, e.g. HBr, is added to remove the protecting carbethoxy group and to obtain the desired acid addition salt in one single step.

In one embodiment, compound I is

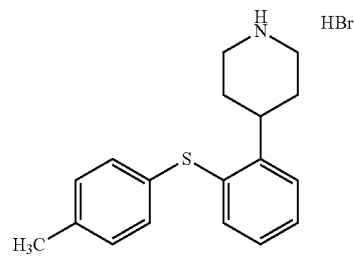 [SMILES: Br ; Cc1ccc(Sc2ccccc2C2CCNCC2)cc1]

which is obtained by dissolving 1 equivalent of

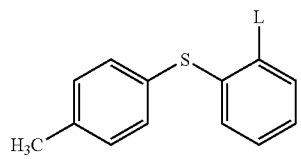

in heptanes and THF (typically 0.1-3 equivalents of THF) at a temperature between around 5° C. and around −25° C., such as between around −10° C. and around −25° C., such as around −15° C., upon which n-butyl lithium (1-1.5 equivalent) is added while keeping the temperature below 0° C. Typically, L is Br. Once the addition is completed, the solution is cooled to a temperature between around −10° C. and around −25° C., such as around −15° C. and approximately an equimolar amount of N-benzyl-4-piperidone is added while maintaining the temperature. When addition is completed, the solution is allowed to warm to room temperature.

The reaction is quenched with water, and the product is isolated by phase separation using a suitable solvent, such as ethyl acetate and adjusting the pH of the aqueous phase to 10-12, e.g. by NaOH. The solvent is removed or reduced by distillation, and fresh solvent, such as e.g. THF is added and removed one or more times. Fresh solvent is added and hydrogen chloride gas is bubbled into the solution upon which the compound

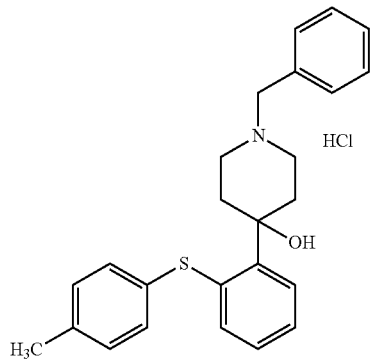 [SMILES: Cc1ccc(Sc2ccccc2C2(O)CCN(Cc3ccccc3)CC2)cc1 ; Cl]

precipitates as crystals after mixing with a suitable anti-solvent, such as di-ethyl ether. As mentioned above, seeding with crystals is an alternative to precipitation by addition of an anti-solvent. 1-benzyl-4-hydroxy-4-[2-(4-methylphenylsulfanyl)phenyl]piperidine, HCl exists in polymorphic forms as discussed later, i.e. an α- and a β-form. A polymorph with the highest melting point is the most stable and also tends to be the least soluble. It is an advantage to seed with a polymorph with low solubility as this will lower the amount of compound that remains in solution, i.e. improve the yield. The polymorph with the highest melting point, i.e. the β-form, is found to be the least soluble in relevant solvents.

One equivalent of said compound is suspended in a solvent, such as acetone together with approximately 2 equivalents of a base, such as $Na_2CO_3$ and 2-3, such as approximately 2.5, equivalents of ethyl chloroformate to obtain the compound

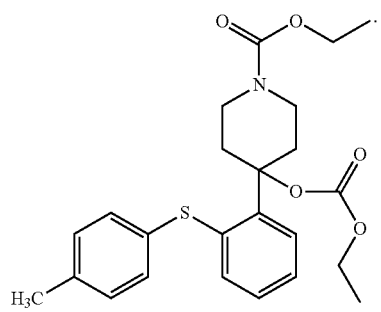 [SMILES: CCOC(=O)OC1(c2ccccc2Sc2ccc(C)cc2)CCN(C(=O)OCC)CC1]

Said compound is worked up by addition of water and a solvent, such as toluene and collection of the organic phase. The solvent is fully or partly removed by distillation and the resulting residue is slowly mixed with to 2-3, such as approximately 2.5, equivalents $Et_3SiH$ in TFA at a temperature between around −10° C. and around −25° C., such as around −15° C. When mixing is completed, the reaction is allowed to warm to room temperature to obtain the compound

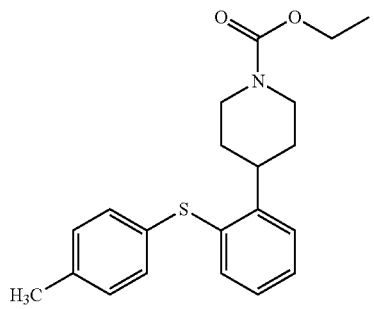 [SMILES: CCOC(=O)N1CCC(c2ccccc2Sc2ccc(C)cc2)CC1]

which compound is worked up by phase separation. Optionally, the organic phase which contains the compound may be refluxed with ethanolamine to capture the benzylchloride released. HBr in acetic acid (1.5-4 equivalents, such as approximately 2 equivalents) is added to achieve the final product. Optionally, additional recrystallisation of the product may be applied at this stage. Suitable solvents include water and alcohols, such as methanol and ethanol.

In one embodiment, the invention provides a process for the manufacture of a compound of the formula

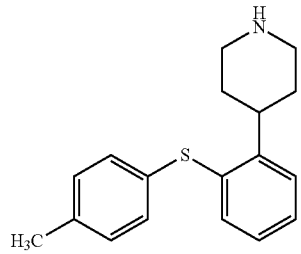 [SMILES: Cc1ccc(Sc2ccccc2C2CCNCC2)cc1]

or acid addition salts thereof, the process comprising the steps of reacting a compound of the formula

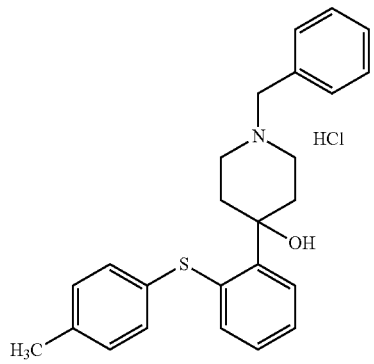 [SMILES: Cc1ccc(Sc2ccccc2C2(O)CCN(Cc3ccccc3)CC2)cc1 ; Cl]

with ethyl chloroformate to obtain a compound of the formula

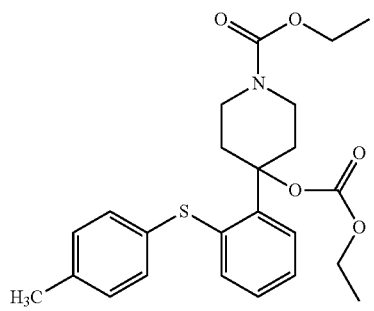 [SMILES: CCOC(=O)OC1(c2ccccc2Sc2ccc(C)cc2)CCN(C(=O)OCC)CC1]

which compound is further reacted with $Et_3SiH$ and trifluoro acetic acid followed by reaction with an acid to remove the N-piperidine protecting group and optionally to obtain a desired acid addition salt. In particular, the hydrobromic acid addition salt can be obtained by reaction with hydrobromic acid in acetic acid to remove the N-piperidine protecting group and to obtain the desired salt in one step.

As shown in the examples, this process for the manufacture of 4-[2-(4-methylphenylsulfanyl)phenyl]piperidine, HBr has an overall yield of above 50%, whereas the manufacturing process using carbethoxy as protecting group only reaches a yield around 25%-45% depending on the temperature. Experiments with the above reactions in the 50-60 kg scale suggest that the difference in yield is even more pronounced on large scale.

The below compounds have been shown to be particular useful intermediates in the manufacture of [methylphenylsulfanylphenyl]piperidines, such as 4-[2-(4-methylphenylsulfanyl)phenyl]-piperidine and acid addition salts thereof.

i)

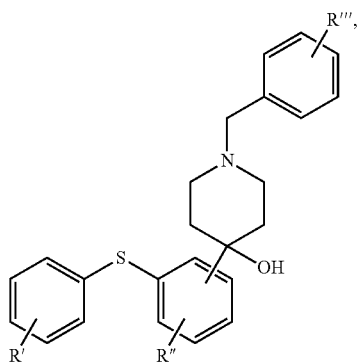

and acid addition salts thereof, and in particular 1-benzyl-4-hydroxy-4-[2-(4-methylphenylsulfanyl)phenyl]piperidine

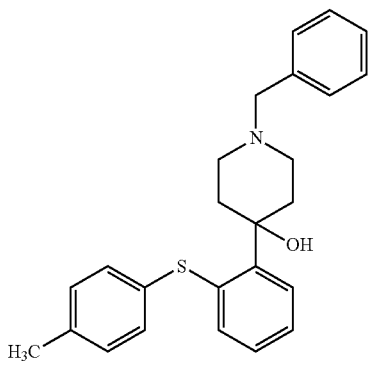 [SMILES: Cc1ccc(Sc2ccccc2C2(O)CCN(Cc3ccccc3)CC2)cc1]

and acid addition salts thereof; and ii)

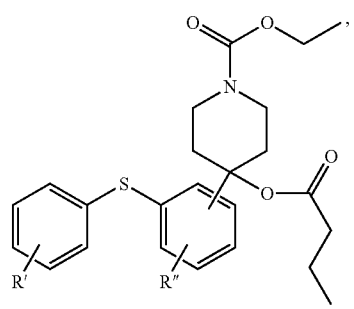

and in particular 4-ethoxycarbonyloxy-4-(2-p-tolylsulfanyl-phenyl)-piperidine-1-carboxylic acid ethyl ester

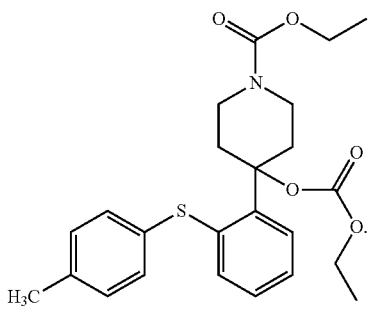 [SMILES: CCOC(=O)OC1(c2ccccc2Sc2ccc(C)cc2)CCN(C(=O)OCC)CC1]

In one embodiment, the invention relates to compound i) or acid addition salts thereof, or compound II).

Figure 2:
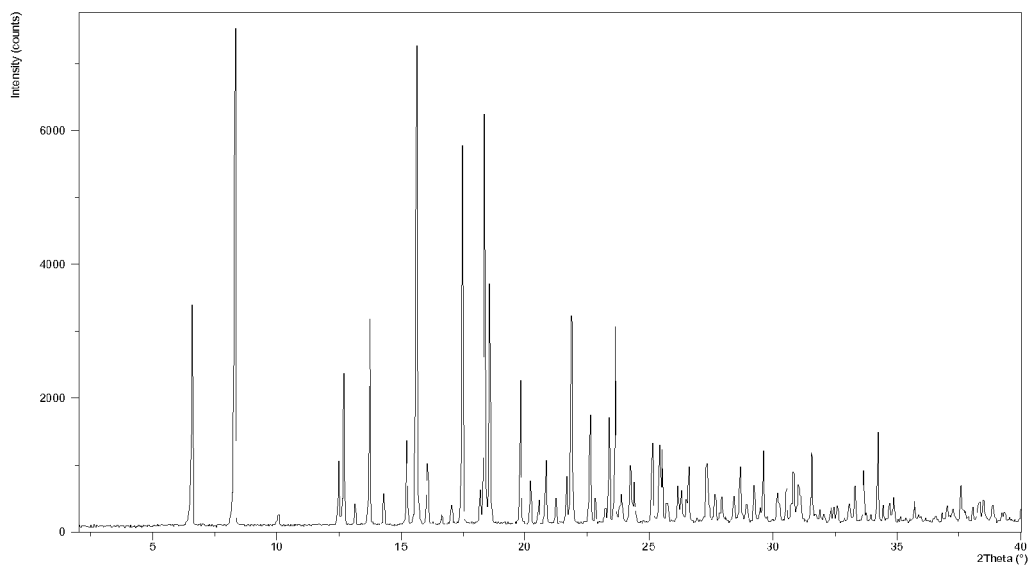
Figure 3:
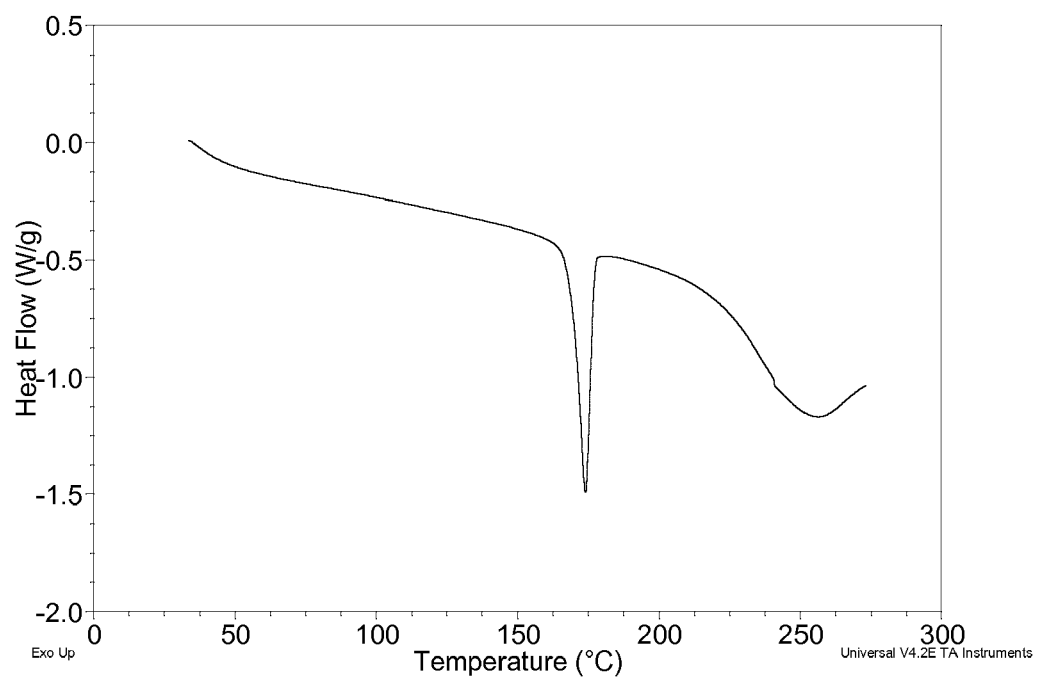
Figure 4:
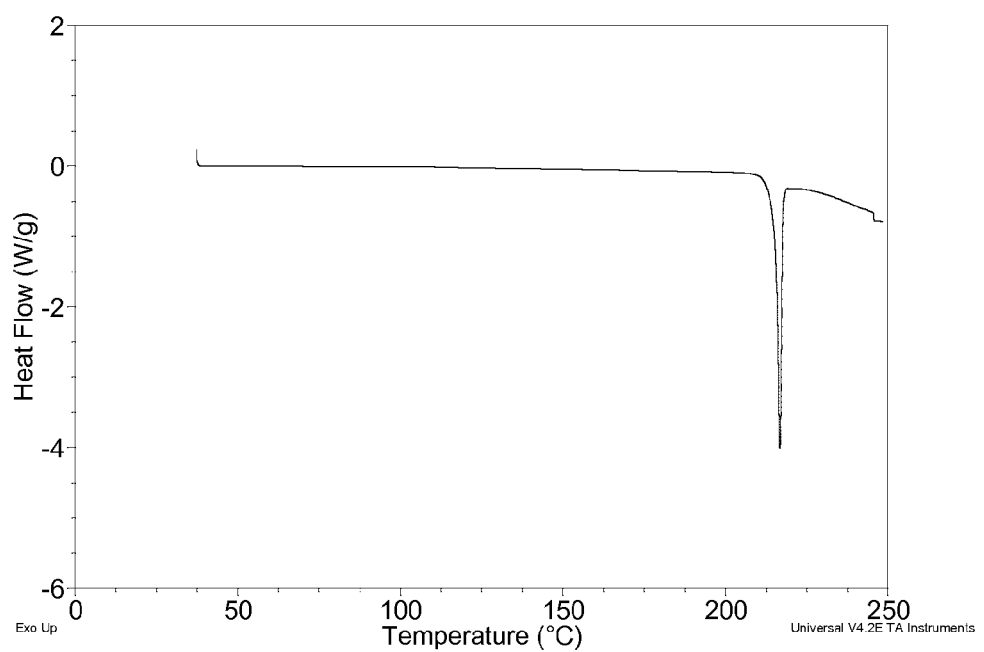

In one embodiment, the invention relates to 1-benzyl-4-hydroxy-4-[2-(4-methylphenylsulfanyl)phenyl]piperidine, HCl in a crystalline form, in particular with XRPD reflections at approximately 4.36, 7.53, 11.51 and 14.08, such as with a XRPD as shown in FIG. 1 (the α-form); or with XRPD reflections at approximately 6.59, 8.33, 12.51 and 13.37, such as with an XRPD as shown in FIG. 2 (the β-form). As shown in FIGS. 3 and 4, the 0020- and the β-form of 1-benzyl-4-hydroxy-4-[2-(4-methylphenylsulfanyl)phenyl]piperidine, HCl have melting points at around 170° C. and around 216° C., respectively. The α-form can be obtained by crystallisation from THF; the β-form by crystallisation for acetone.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context.

EXAMPLES

The melting points are measured using Differential Scanning calorimetry (DSC). The equipment is a TA-Instruments DSC-Q1000 calibrated at 5°/min to give the melting point as onset value. About 2 mg of sample is heated 5°/min in a loosely closed pan under nitrogen flow.

X-Ray powder diffractograms were measured on a PANalytical X'Pert PRO X-Ray Diffractometer using CuK$_{\alpha 1}$ radiation. The samples were measured in reflection mode in the 2θ-range 5-40° using an X'celerator detector. Difraction data are indicated ±0.1 (°2θ)

Example 1
2-(4-tolylsulfanyl)-phenyl bromide

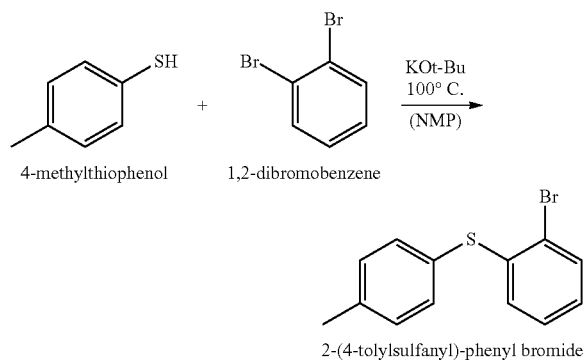

To a stirred solution of potassium tert-butoxide (75 g, 0.668 mol, 1.1 eq) in N-methyl-2-pyrrolidone (225 mL) a solution of 4-methylthiophenol (78 g, 0.628 mol, 1.0 eq) dissolved in N-methyl-2-pyrrolidone (225 mL) was added. To the reaction mixture was then added to 1,2-dibromobenzene (73 mL, 605 mol, 1.0 eq); once the addition was complete the reaction mixture was warmed to 100° C. and maintained at this temperature for approximately 22 hrs. (The reaction is monitored by HPLC). After cooling to room temperature water (750 mL) and toluene (375 mL) were added, the phases separated, and the water phase extracted with toluene (250 mL). The organic phases were combined and the organic phase was concentrated by vacuum distillation. Once the distillation was complete, the residue was cooled and methanol (750 mL) added. The solvents were removed from the organic phase by vacuum distillation and further methanol (250 mL) added. Stirring over night at room temperature precipitated 2-(4-tolylsulfanyl)-phenyl bromide which was isolated by filtration, washed with methanol (260 mL) and dried in vacuum. Yield=120.8 g.

Example 2
1-benzyl-4-hydroxy-4-[2-(4-methylphenylsulfanyl)phenyl]piperidine, HCl

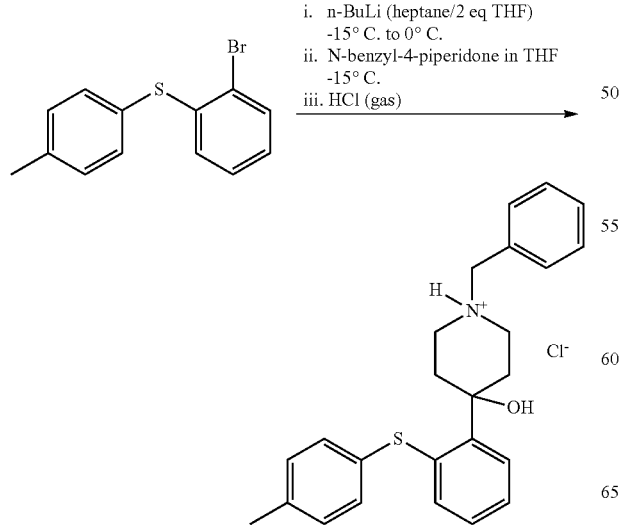

2-(4-tolylsulfanyl)-phenyl bromide (419 g, 1.5 mol) was dissolved in heptanes (900 mL) and dry tetrahydrofuran (243 mL, 3 mol), and after 0.5 h the reaction mixture was cooled down to −15° C. under an atmosphere of nitrogen. To this mixture was added n-butyl lithium in heptanes 2.7 M (583 mL, 1.6 mol) while maintaining the temperature in the range −15° C. to 0° C. Once the addition was complete the reaction mixture was cooled to around −15° C. before a solution of N-benzyl-4-piperidone (278 mL, 1.5 mol) in dry tetrahydrofuran (450 mL) was added at such a rate that the temperature did not rise above −15° C. Once the addition was complete the reaction was allowed to warm to room temperature.

The reaction was quenched with water (1 L), and ethyl acetate (1 L) and aqueous sodium hydroxide solution (1 M, 300 mL) added. The pH was maintained between 10 and 12. The phases were separated, the water phase was extracted with ethyl acetate (1 L), and the organic phases combined. The solvents were removed by vacuum distillation (max. temperature 50° C.). Once the distillation was complete, tetrahydrofuran (2.25 L) was added and the solvents removed by vacuum distillation (max. temperature 50° C.). Once the distillation was complete, tetrahydrofuran (2 L) was added. Hydrogen chloride gas (85 g, 2.33 mol), was bubbled into the solution and the product precipitated by addition to diethyl ether (9 L) with stirring. The precipitate was filtered off and washed with diethyl ether (1.2 L) and the precipitate dried in a vacuum oven over night (T=50° C.) to obtain the title compound at 574 g (90% yield).

Example 3
4-[2-(4-methylphenylsulfanyl)phenyl]piperidine, HBr

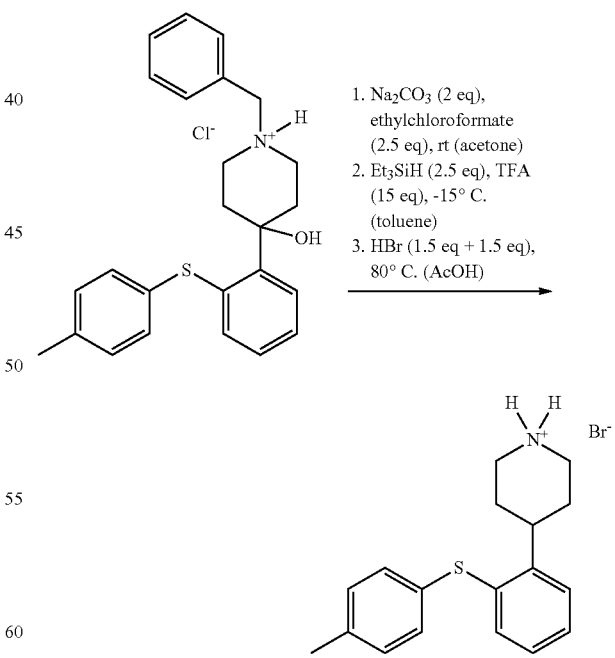

After stirring a suspension of 1-benzyl-4-hydroxy-4-[2-(4-methylphenylsulfanyl)phenyl]-piperidine, HCl (426 g, 1 mol) and sodium carbonate (212 g, 2 mol) in acetone (2 L) for 1 hr, ethyl chloroformate (240 mL, 2.5 mol) was added. After stirring for a further 60 minutes, toluene (3 L) and water (3.5

L) were added and the reaction mixture stirred. The phases were separated and the organic phase washed with 2 L 2 M aq. hydrogen chloride solution. Solvent (approx 3 L) was removed by distillation ($T_{max\ distillation}$=120° C.). The resulting solution was added slowly to a mixture of trifluoro acetic acid (1.11 L, 15 mol) and triethylsilane (400 mL, 2.5 mol, 2.5 eq) at −15° C. Once the addition was complete the reaction mixture was allowed to warm to room temperature before water (4 L) and toluene (3.5 L) were added. The mixture was stirred for 30 minutes before the phases were separated, the organic phase washed with water (3 L), and ethanolamine (300 mL, 5 mol) added to the organic phase. The organic phase was refluxed over night before 2 M aqueous hydrogen chloride solution (2.5 L) was added and the mixture stirred for 30 min. The phases were separated and the organic phase washed with hydrogen chloride solution (1.5 L, 2 M). The solvents were distilled off the organic phase at a maximum temperature of 130° C. To the remaining solution was added hydrogen bromide in acetic acid (350 mL, 5.7 M, 2 mol), and the reaction mixture was heated at 80° C. over night. The reaction was cooled down to room temperature and hydrogen bromide (350 mL, 5.7 M in acetic acid, 2 mol) added and the reaction mixture warmed at 80° C. for 4 hrs before cooling to room temperature. Diethyl ether (2 L) was added, and the reaction mixture stirred over night before the precipitate was filtered off and washed with 1 L diethyl ether. The precipitate was re-crystallised from 2-propanol to yield 208 g of the title compound (57%).

Example 4

1-tert-butoxy-carbonyl-4-hydroxy-4-[2-(4-methylphenyl-sulfanyl)phenyl]piperidine at −78° C.

See WO 03/029232 page 18.

Example 5

1-carbethoxy-4-hydroxy-4-[2-(4-methylphenylsulfanyl)phenyl]piperidine at −15° C.

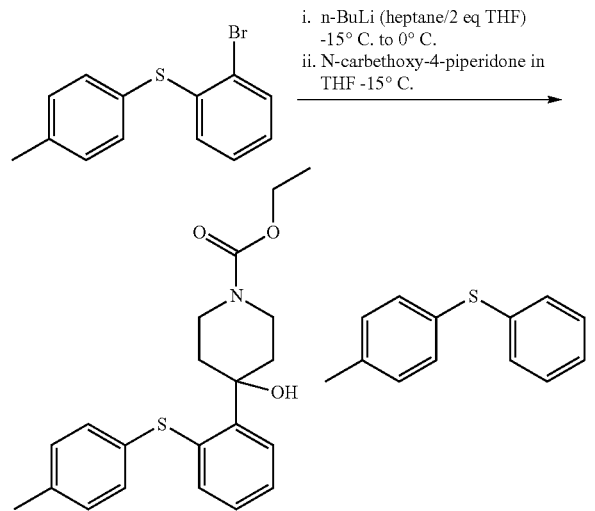

2-(4-tolylsulfanyl)-phenyl bromide (6.98 g, 25 mmol) was dissolved in heptanes (40 mL) and dry tetrahydrofuran (4.1 mL) and after 1.5 hrs the reaction mixture was cooled down to 0° C. under an atmosphere of nitrogen. n-Butyllithium in heptanes 2.7 M (9.8 mL, 26.5 mmol) was added at 0° C. and after 45 min the reaction mixture was cooled to −15° C. A solution of N-carbethoxy-4-piperidone (3.8 mL, 25 mmol) in tetrahydrofuran (15 mL) was added maintaining the temperature below −15° C. Once the addition was complete the reaction was allowed to warm to room temperature. The reaction was quenched with a dilute hydrogen chloride solution. A sample from the organic phase shows a ratio of 1-carbethoxy-4-hydroxy-4-[2-(4-methylphenylsulfanyl)phenyl]piperidine to 1-methyl-4-phenylsulfanyl-benzene of 28:58.

Example 6

1-carbethoxy-4-hydroxy-4-[2-(4-methylphenylsulfanyl)phenyl]piperidine at −40° C.

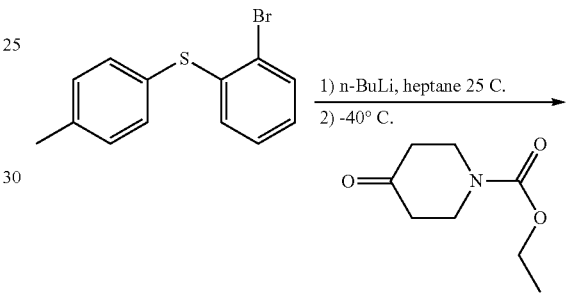

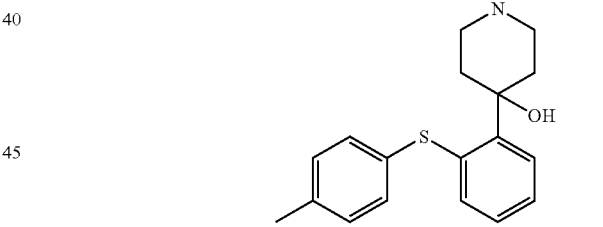

In anhydrous equipment under a nitrogen atmosphere was stirred a mixture of 2-(4-tolylsulfanyl)-phenyl bromide (600 g, 2.15 mol) in heptanes (4.5 L) at room temperature (25° C.). n-Bu-lithium (10 M, 236 mL) solution in heptane was then added by canulation. After stirring at room temperature for 30 minutes the reaction mixture was cooled to −50° C. before a solution of carbetoxypiperidone in THF (1.5 L) was added dropwise while maintaining the temperature under −40° C. Once the addition was completed, reaction was allowed to warm to 0° C. before dilute HCl (1 L) was added maintaining the temperature below 10° C. Once addition was complete reaction was stirred for a further 15 minutes before phases where allowed to separate. Phases were separated, the water layer was extracted with ethyl acetate (1 L) and the organic layers combined. The combined organic layer was washed with NaCl solution (15%) (1 L), dried over magnesium sulphate, evaporated to dryness and slurried in diethyl ether (250 mL) for 30 minutes, filtered and dried at 40° C. in a vacuum oven. Yield 55-60%.

Example 7

1-benzoyl-4-hydroxy-4-[2-(4-methylphenylsulfanyl)phenyl]piperidine at −15° C.

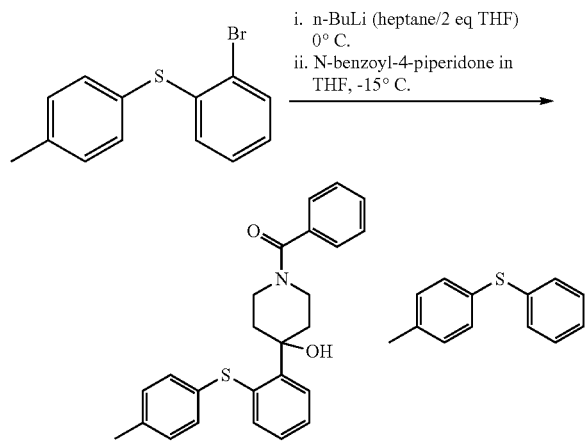

2-(4-tolylsulfanyl)-phenyl bromide (6.98 g, 25 mmol) was dissolved in heptanes (40 mL) and dry tetrahydrofuran (4.1 mL) and after 1.5 hrs the reaction mixture was cooled down to 0° C. under an atmosphere of nitrogen. n-Butyl lithium in heptanes 2.7 M (9.8 mL, 26.5 mmol) was added at 0° C. and after 45 minutes the reaction mixture was cooled to −15° C. A solution of N-benzyloxy-4-piperidone (5.08 g, 25 mmol) in dry tetrahydrofuran (40 mL) was added to the reaction mixture maintaining the temperature below −15° C. Once the addition was complete the reaction was allowed to warm to room temperature before quenching with dilute aqueous HCl solution. HPLC indicated the presence of 1-methyl-4-phenylsulfanyl-benzene and a complex mixture of unknown compounds.

Example 8

4-[2-(4-methylphenylsulfanyl)phenyl]piperdidine, HBr

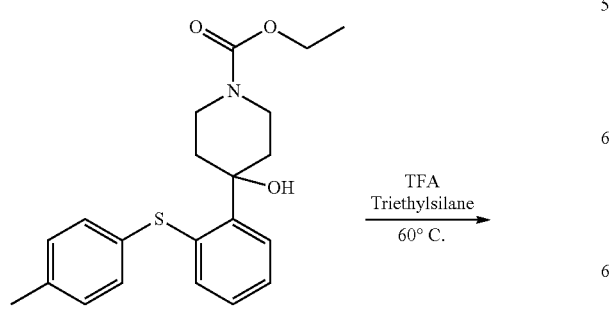

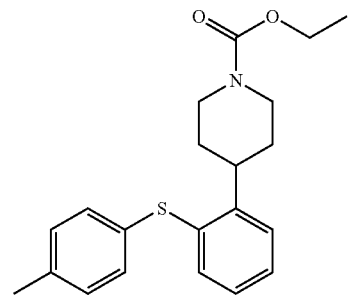

To a stirred suspension of 1-carbethoxy-4-hydroxy-4-[2-(4-methylphenylsulfanyl)-phenyl]piperidine (462 g, 1.244 mol) in triethyl silane (362 g, 3.1 mol) was added trifluoro acetic acid (2835 g, 24.9 mol). The reaction mixture was then heated at 60° C. for 18 hrs before cooling to 0° C. To the cooled solution was added toluene (750 mL) and then water (750 mL) followed by stirring for 20 minutes. The reaction mixture was allowed to stand without stirring for 60 min, the organic phase separated, and the water phase re-extracted with toluene (750 ml). The toluene was removed under reduced pressure to give the crude product as an oil.

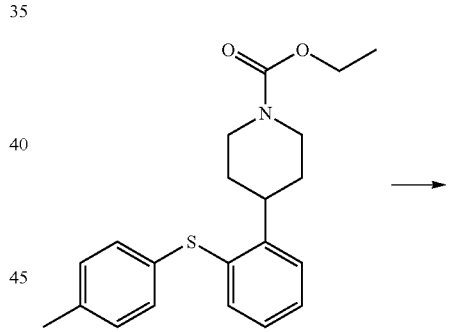

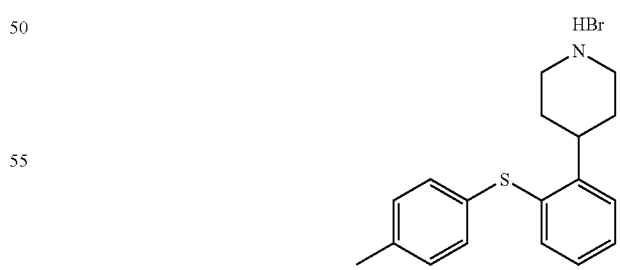

The crude oil from the previous step was warmed in a mixture of acetic acid HBr at 80° C. (Reaction complete after 18 hrs). The reaction mixture was allowed to cool to room temperature and diethyl ether (800 mL) was added and stirred for a further 60 minutes. The product was isolated by filtration, washed with cold ether (300 mL), and dried in vacuo. Yield=80%.

Example 9

4-ethoxycarbonyloxy-4-(2-p-tolylsulfanyl-phenyl)-piperidine-1-carboxylic acid ethyl ester

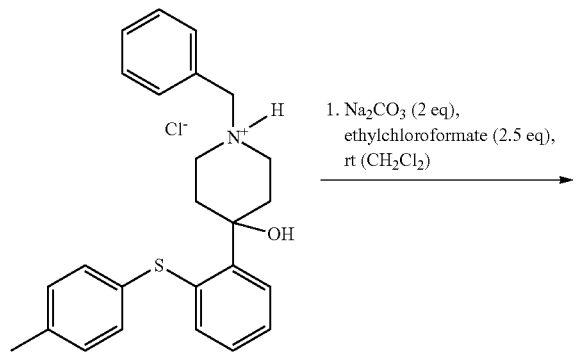

A suspension of 1-benzyl-4-hydroxy-4-[2-(4-methylphenylsulfanyl)phenyl]piperidine, HCl (42.6 g, 100 mmol) and sodium carbonate 21.2 g (200 mmol, 2 eq) in dichloromethane (400 mL) was stirred at room temperature for approximately 90 minutes before ethyl chloroformate (24 mL, 250 mmol) was added. After 60 minutes water (400 mL) was added and the phases separated. The organic phase was washed with first dilute aqueous HCl, followed by a dilute sodium hydroxide solution and brine. The organic phase was dried over MgSO$_4$, filtered and the solvent removed under reduced pressure. Diethyl ether (200 mL) was added and the mixture stirred overnight at room temperature. The title compound was isolated by filtration, washed with diethyl ether (80 mL) and dried over night in a vacuum oven at 50° C. Yield=20.15 g (45%).

NMR Data

The following NMR data were obtained for the synthesised compounds 4-ethoxycarbonyloxy-4-(2-p-tolylsulfanyl-phenyl)-piperidine-1-carboxylic acid ethyl ester $^{13}$C-NMR (d$^6$-DMSO, 125.8 MHz):
155.0 (s), 152.4 (s), 140.8 (s), 138.3 (s), 135.4 (s), 133.4 (d), 131.19 (d), 130.9 (s), 130.8 (d), 128.5 (d), 127.1 (d), 126.4 (d), 81.9 (s), 63.6 (t), 61.2 (t), ca. 39.9 (t), 33.4 (t), 21.0 (q), 14.9 (q), 14.5 (q) ppm.

4-[2-(4-methylphenylsulfanyl)phenyl]piperdidine, HBr $^{13}$C-NMR (D$_2$O, 125.8 MHz):
145.0 (s), 137.5 (s), 134.3 (s), 132.5 (d), 131.7 (s), 131.5 (d), 130.6 (d), 128.5 (d), 127.9 (d), 126.7 (d), 44.0 (t), 36.7 (d), 29.1 (t), 21.0 (q) ppm.

1-benzyl-4-hydroxy-4-[2-(4-methylphenylsulfanyl)phenyl]piperidine, HCl $^{13}$C-NMR (d$^6$-DMSO, 125.8 MHz):
144.7 (s), 138.1 (s), 137.5 (s), 133.8 (d), 132.3 (s), 132.0 (d), 131.6 (d), 130.7 (d), 130.1 (s), 129.8 (d), 129.1 (d), 128.2 (d), 126.0 (d), 125.9 (d), 69.4 (s), 59.1 (t), 47.8 (t), 32.7 (t), 21.1 (q).

2-(4-tolylsulfanyl)-phenyl bromide $^{13}$C-NMR (d$^6$-DMSO, 125.8 MHz):
139.5 (s), 139.0 (s), 134.4 (d), 133.3 (d), 131.2 (d), 128.8 (d), 128.0 (s), 127.9 (d), 121.6 (s), 21.2 (q).

Example 10

1-benzyl-4-hydroxy-4-[2-(4-methylphenylsulfanyl)phenyl]piperidine, HCl

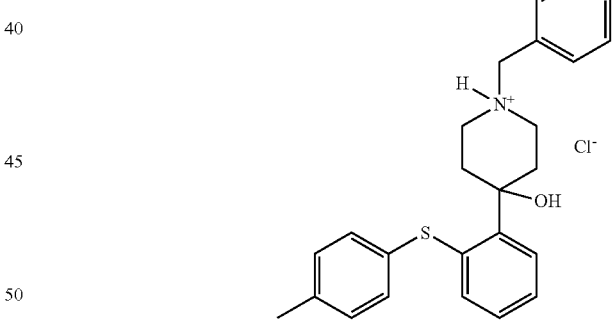

149.7 kg 2-(4-tolylsulfanyl)-phenyl bromide (536 mol) was suspended in 282 kg heptane and 19.5 kg dry tetrahydrofuran (270 mol, 0.5 eq) and the reaction mixture was cooled down to −15° C. 143.8 kg 25% n-butyl lithium in heptane (561 mol, 1.05 eq) was added at temperatures between −15° C. to −5° C. following which the temperature was lowered to −15° C. 104.5 kg N-benzyl-4-piperidone (552 mol, 1 eq) dissolved in 79 kg (1096 mol, 2 eq) dry tetrahydrofuran was added at below −15° C., and the reaction was allowed to come to room temperature. 360 L water, 320 kg ethyl acetate and 25 L 27.7% aq. sodium hydroxide solution were added, the phases separated, and solvents removed from the organic phase by vacuum distillation (max. temperature 39° C.). 543 L tetrahydrofuran was added, and solvents removed by vacuum distillation (max. temperature 43° C.), following

Example 11

4-[2-(4-methylphenylsulfanyl)phenyl]piperdidine, HBr

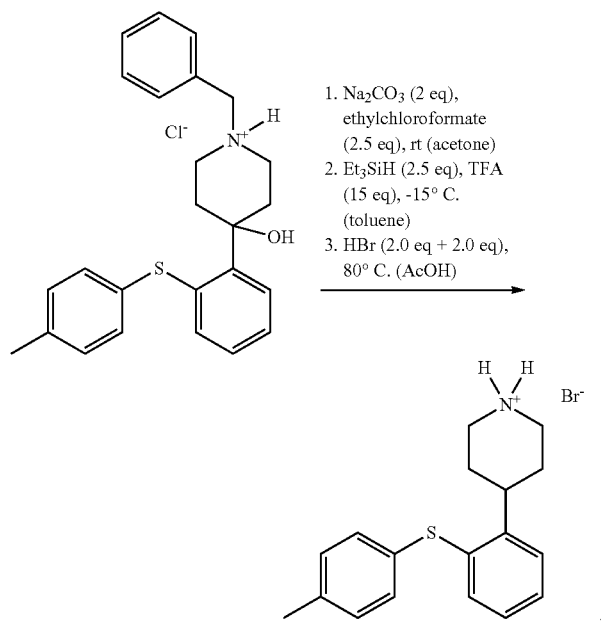

42.6 g (0.1 mol) 1-benzyl-4-hydroxy-4-[2-(4-methylphenylsulfanyl)phenyl]piperidine, HCl and 21.2 g (0.2 mol, 2 eq) sodium carbonate were suspended in 0.2 L acetone, and after stirring for 1.5 h at room temperature the gas evolution ceases and 24 mL (0.25 mol, 2.5 eq) ethyl chloroformate was added and the reaction was stirred over night. 0.3 L toluene and 0.35 L water were added and the phases were separated. The organic phase was washed with 0.2 L 20% aq. acetic acid. The organic phase was collected and 0.33 L solvent distilled off 111 mL (1.5 mol, 15 eq) trifluoro acetic acid and 40 mL (0.25 mol, 2.5 eq) triethylsilane were mixed and cooled down to −15° C. The toluene solution was added to the trifluoro acetic acid/triethylsilane mixture so that the temperature does not rise above −15° C., after which the temperature is allowed to increase to room temperature. 0.4 L water and 0.35 L toluene were added, the phases separated, and the organic phase washed with 0.3 L water. 30 mL (0.5 mol, 5 eq) 2-ethanolamine was added to the organic phase which was refluxed over night, and washed with 0.25 L 2 M aq. hydrogen chloride solution. The phases were separated and the organic phase washed with 75 mL 2 M aq. hydrogen chloride solution. The organic phase was filtered over a filter cloth, the solvents distilled off, and to the remaining solution was added 35 mL 5.7 M hydrogen bromide in acetic acid (0.2 mol, 2 eq). The mixture was heated to 80° C. over night. The reaction was cooled to room temperature, 35 mL 5.7 M hydrogen bromide in acetic acid (0.2 mol, 2 eq) added, and the reaction mixture warmed at 80° C. for 4 h. The reaction mixture was cooled to room temperature, and the solvents distilled off 50 mL 2-propanol and 20 mL acetic acid were added and the reaction refluxed. The mixture was allowed to cool to room temperature, and the resulting precipitate filtered and washed with 50 mL 2-propanol and dried. The dried solid was dissolved in 135 mL boiling water, the mixture allowed to cool to room temperature, and the resulting precipitate was filtered, washed with 20 mL water and dried to give 27.0 g of the title compound (74% yield).

The invention claimed is:

1. A process wherein a compound of formula II

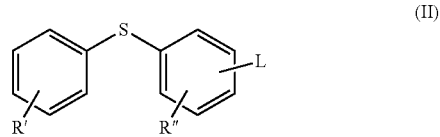

wherein R' and R" independently represent one, two or three hydrogen, halogen, or $C_{1-6}$-alkyl and L represents a leaving group is reacted with an optionally substituted N-benzyl-4-piperidone

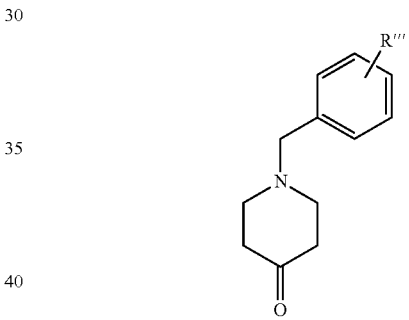

wherein R'" represents hydrogen or —O—$C_{1-6}$-alkyl, to obtain a compound of formula III

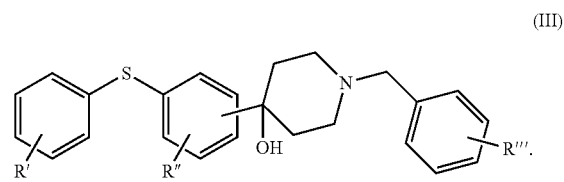

2. The process according to claim 1, wherein a compound of formula II

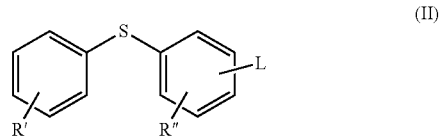

wherein R' and R" independently represent one, two or three hydrogen, halogen, or $C_{1-6}$-alkyl and L represents a leaving group is reacted with a metallation agent selected from alkyl lithium, alkyl magnesium or magnesium and an optionally substituted N-benzyl-4-piperidone

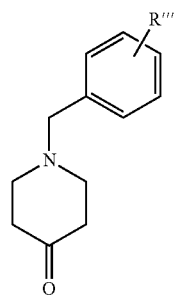

wherein R''' represents hydrogen or —O—$C_{1-6}$-alkyl, at a temperature between around −25° C. and around 5° C. to obtain a compound of formula III (III)

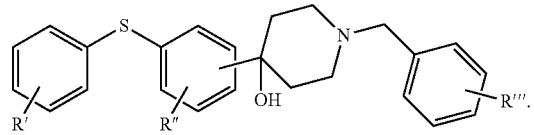

3. The process according to claim 1, wherein R' is 4-methyl and R'' is hydrogen.

4. The process according to claim 1, wherein R''' is hydrogen.

5. The process according to claim 2, wherein the metallation agent is n-butyl lithium.

6. A process for the manufacture of compound I (I)

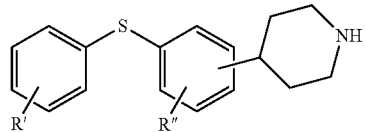

and acid addition salts thereof, wherein R' and R'' independently represent one, two or three hydrogen, halogen, or $C_{1-6}$-alkyl, said process comprising the steps of reacting a compound of formula II (II)

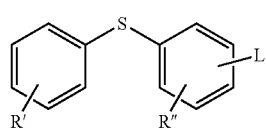

wherein L represents a leaving group, with an optionally substituted N-benzyl-4-piperidone

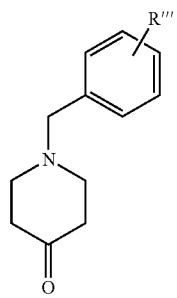

wherein R''' represents hydrogen or O—$C_{1-6}$-alkyl, to obtain a compound of formula III (III)

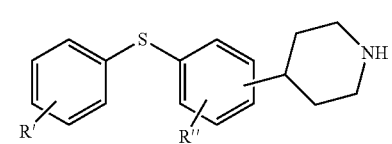

7. The process according to claim 6 for the manufacture of compound I (I)

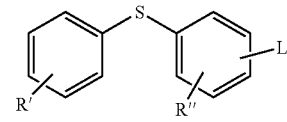

and acid addition salts thereof, wherein R' and R'' independently represent one, two or three hydrogen, halogen, or $C_{1-6}$-alkyl, said process comprising the steps of reacting a compound of formula II (II)

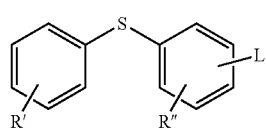

wherein L represents a leaving group, with a metallation agent selected from alkyl lithium, alkyl magnesium or magnesium and an optionally substituted N-benzyl-4-piperidone

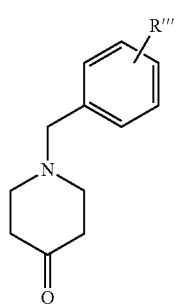

wherein R''' represents hydrogen or O—$C_{1-6}$-alkyl, at a temperature between −25° C. and 5° C. to obtain a compound of formula III

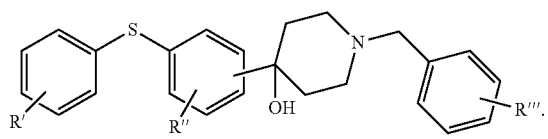

(III)

8. The process according to claim 6, wherein R' is 4-methyl and R'' is hydrogen.

9. The process according to claim 6, wherein R''' is hydrogen.

10. The process according to claim 7, wherein the metallation agent is n-butyl lithium.

11. The process according to claim 6, wherein compound II is

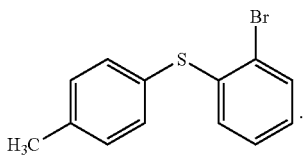

12. The process according to claim 6, wherein said salt is the hydrobromic acid addition salt.

13. The process according to claim 6, wherein compound I is

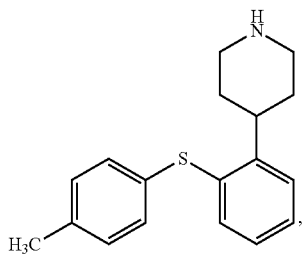 [SMILES: Cc1ccc(Sc2ccccc2C2CCNCC2)cc1]

or acid addition salts thereof said process comprising the steps of reacting

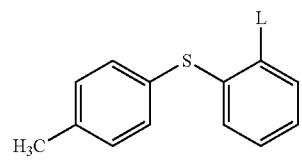

with n-butyl lithium at a temperature below 0° C. followed by reaction with N-benzyl-4-piperidone at a temperature between around 5° C. and around −25° C. and HCl to obtain a compound of the formula

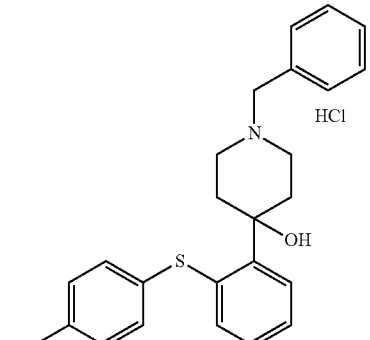

which compound is further reacted with ethyl chloroformate to obtain a compound of the formula

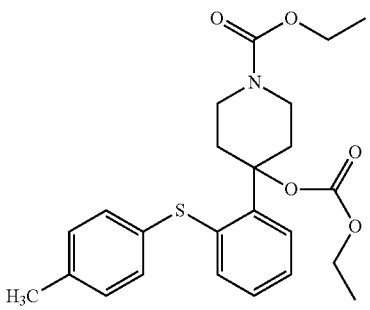 [SMILES: CCOC(=O)OC1(c2ccccc2Sc2ccc(C)cc2)CCN(C(=O)OCC)CC1]

which compound is further reacted with $Et_3SiH$ and trifluoro acetic acid followed by reaction with an acid to remove the N-piperidine protecting group and optionally to obtain a desired acid addition salt.

14. The process according to claim 13, wherein L is Br.

15. The process according to claim 13, wherein said salt is the hydrobromic acid addition salt and wherein the N-protecting group is removed by reaction with hydrobromic acid in acetic acid.

16. A process for the manufacture of a compound of the formula

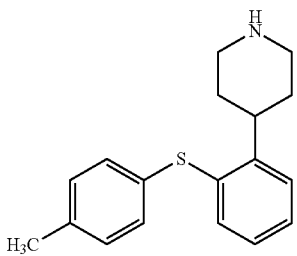 [SMILES: Cc1ccc(Sc2ccccc2C2CCNCC2)cc1]

or acid addition salts thereof, the process comprising the steps of reacting a compound of the formula

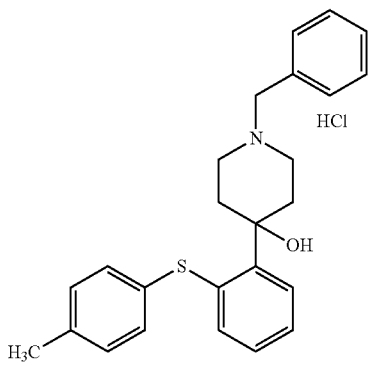 [SMILES: Cc1ccc(Sc2ccccc2C2(O)CCN(Cc3ccccc3)CC2)cc1 ; Cl]

with ethyl chloroformate to obtain a compound of the formula

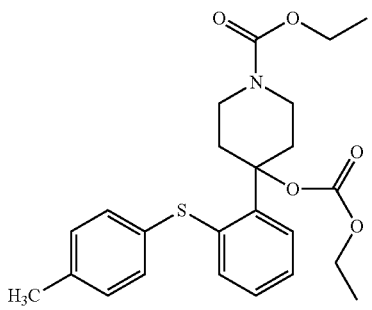 [SMILES: CCOC(=O)OC1(c2ccccc2Sc2ccc(C)cc2)CCN(C(=O)OCC)CC1]

which compound is further reacted with Et₃SiH and trifluoro acetic acid followed by reaction with an acid to remove the N-piperidine protecting group and optionally to obtain a desired acid addition salt.

17. The process according to claim 16, wherein said salt is the hydrobromic acid addition salt and wherein the N-protecting group is removed by reaction with hydrobromic acid in acetic acid.

18. The process according to claim 14, wherein the compound

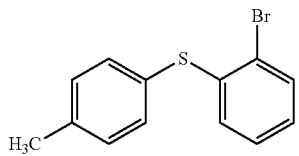

is prepared in an initial step which 4-methylthiophenol and 2-iodobromobenzene are reacted in the presence of palladium source and a bidentate phosphine ligand at basic pH at elevated temperatures.

* * * * *